United States Patent [19]
Cook et al.

[11] Patent Number: 5,138,045
[45] Date of Patent: Aug. 11, 1992

[54] POLYAMINE CONJUGATED OLIGONUCLEOTIDES

[75] Inventors: Philip D. Cook; Charles J. Guinosso, both of Carlsbad, Calif.

[73] Assignee: ISIS Pharmaceuticals, Carlsbad, Calif.

[21] Appl. No.: 558,663

[22] Filed: Jul. 27, 1990

[51] Int. Cl.$^5$ .............................................. C07H 17/00
[52] U.S. Cl. ................................................ 536/27
[58] Field of Search ......................................... 536/27

[56] References Cited

PUBLICATIONS

Beaucage, S. L. et al., *J. Am. Chem. Soc.* 112:1253–1254 (1990).
Ceruzzi, M. and Draper, K. *Nucleosides & Nucleotides* 8:815–818 (1989).
Lemaitre, M., Baynard, B. and LeBleu, B. *Proc. Natl. Acad. Sci. U.S.A.* 84:648–652 (1987).
Letsinger, et al. *Proc. Natl. Acad. Sci. U.S.A.* 86:653–656 (1989).
Loke, S. L., Stein, C., Zhang, X. H. Avigan, M., Cohen, J. and Neckers, L. M. *Curr. Top. Microbiol. Immunol.* 141:282–289 (1988).
Loke et al, *Proc. Natl. Acad. Sci. U.S.A.* 86:3473–3478 (1989).
Loke, S. L., Stein, C. A., Zhang, X. H., Mori, K., Nakanishi, J., Subashinghe, G., Cohen, J. S. and Neckers, L. M. *Proc. Natl. Acad. Sci. U.S.A.* 86:3473–3479 (1989).
Marcus-Sekura, C. H., Woerner, A. M., Shinozuka, K. Zon, G., and Quinman, G. V., *Nuc. Acids Res.* 15:5749–5763 (1987).
Miller, P. S., Braiterman, L. T. and Ts'O, P. O. P., *Biochemistry* 16:1988–1996 (1977).
Miller, P. S., McParland, K. B., Hayerman, K. and Ts'O, P. O. P., *Biochemistry* 20:1874–1880 (1981).
Niitsu and Samejima, *Chem. Pharm. Bull.* 34(3):1032–1038 (1986).
Overman, et al, *Tetrahedron Lett.* 27:4391–4394 (1986).
Pfitzner, K. E. et al., *J. American Chem. Soc.* 85: 3027 (1963).
Stevenson, M. and Iversen, P. L. *J. Gen. Virol* 70:2673–2682 (1989).
Wilson, D. B. *Ann. Rev. Biochem.,* 47:933–965 (1978).
Wu, G. Y. and Wu, C. H. *Biochemistry* 27:887–892 (1988).
Zon, G., *Oligodeoxynucleotides: Antisense Inhibitors of Gene Expression* 234–247, ed. J. S. Cohen (CRC Press, Boca Raton, Fla., 1989).
Nelson, et al., Nucleic Acid Res. 17:7179, 1989.

*Primary Examiner*—John W. Rollins
*Attorney, Agent, or Firm*—Woodcock Washburn Kurtz Mackiewicz & Norris

[57] ABSTRACT

Oligonucleotide analogs are provided having improved cellular uptake and improved nuclease resistance. Modification of oligonucleotides through the attachment of nitrogenous moieties, especially polyamines, hydrazines and the like to nucleosidic portions of the analogs is disclosed. Oligonucleotides targeted at the tat region of HIV comprise certain preferred embodiments.

11 Claims, 2 Drawing Sheets

POLYAMINE CONJUGATED OLIGONUCLEOTIDES

FILED OF THE INVENTION

This invention relates to the field of therapeutics, and in particular to the treatment of infection by antisense therapy. This invention also relates to the field of gene expression. Novel polyamine conjugated phosphorothioate oligonucleotides which are useful in antisense therapy are provided. These oligonucleotides have enhanced cellular uptake and consequently enhanced biological and therapeutic activity. The invention also provides methods of synthesis of novel polyamine conjugated phosphorothioate oligonucleotides.

BACKGROUND OF THE INVENTION

It is well known that most of the bodily states in mammals including most disease states, are effected by proteins. Such proteins, either acting directly or through their enzymatic functions, contribute in major proportion to many diseases in animals and man. Classical therapeutics has generally focused upon interactions with such proteins in efforts to moderate their disease causing or disease potentiating functions. Recently, however, attempts have been made to moderate the actual production of such proteins by interactions with molecules that direct their synthesis, intracellular RNA. These interactions involved the binding of complementary "antisense" oligonucleotides or their analogs to the transcellular RNA in a sequence specific fashion such as by Watson-Crick base pairing interactions.

The pharmacological activity of antisense oligonucleotides, as well as other therapeutics, depends on a number of factors that influence the effective concentration of these agents at specific intracellular targets. One important factor is the stability of the oligonucleotide in the presence of nucleases. Another key factor is the ability of antisense compounds to traverse the plasma membrane of specific cells involved in the disease process.

Cellular membranes consist of lipid protein bilayers that are freely permeable to small, nonionic, lipophilic compounds and inherently impermeable to most natural metabolites and therapeutic agents. Wilson, D. B. Ann. Rev. Biochem. 47:933-965 (1978). The biological antiviral effects of natural and modified oligonucleotides in cultured mammalian cells have been well documented, so it appears that these agents can penetrate membranes to reach their intracellular targets. Uptake of antisense compounds into a variety of mammalian cells, including HL-60, Syrian Hamster fibroblast, U937, L929, CV-1, and ATH8 cells has been studied using natural oligonucleotides and nuclease resistant analogs, such as alkyl triesters, Miller, P. S., Braiterman, L. T. and Ts'O, P. O. P., Biochemistry 16:1988-1996 (1977); methylphosphonates, Marcus-Sekura, C. H., Woerner, A. M., Shinozuka, K. Zon, G., and Quinman, G. V., Nuc. Acids Res. 15:5749-5763 (1987) and Miller, P. S., McParland, K. B., Hayerman, K. and Ts'O, P. O. P., Biochemistry 20:1874-1880 (1981); and phosphorothioates, Ceruzzi, M. and Draper, K. Nucleosides & Nucleotides 8:815-818 (1989); Miller, P. S., Braiterman, L. T. and Ts'O, P. O. P. Biochemistry 16:1988-1996 (1977) and Loke, S. L., Stein, C., Zhang, X. H. Avigan, M., Cohen, J. and Neckers, L. M. Curr. Top. Microbiol. Immunol. 141:282-289 (1988).

Phophorothioates are oligonucleotide analogs in which the oxygen atom in each phosphate linkage is replaced by a sulfur. Although the overall charge is conserved, and they are therefore comparable in that respect to phosphodiester oligonucleotides, several properties of this class of analogs makes them more attractive than other modified compounds. These include ease of chemical synthesis, good aqueous solubility, relatively high resistance to nucleases, and the ability to form stable duplexes with complementary DNA or RNA strands. However, phosphorothioates were studied concurrently with natural compounds by Loke et al, Proc. Natl. Acad. Sci. U.S.A. 86:3473-3478 (1989), and while they may be useful due to their nuclease resistance, they are less efficiently internalized than their natural oligonucleotide counterparts.

Advances in nucleotide chemistry have allowed attachment of functional groups to the 3' and 5' end of the oligonucleotides to enhance cellular uptake in specific cell types. Previous studies have shown that plasmid DNA complexed with an asiaglycoprotein-poly(L-lysine) conjugate, could be targeted to hepatocytes, which contain unique cell surface receptors for galactose-terminal (asialo)glycoproteins. Wu, G. Y. and Wu, C. H. Biochemistry 27:887-892 (1988). Other groups have synthesized oligodeoxyribonucleotides that have a 5'-attached alkylating agent and a 3' attached cholesterol moiety and determined that these modified oligonucleotides were taken up into cells more efficiently than control compounds without the steroid moiety. Zon, G. in Oligodeoxynucleotides: Antisense Inhibitors of Gene Expression 234-247, ed. J. S. Cohen (CRC Press, Boca Raton FL, 1989). Letsinger, et al. Proc. Natl. Acad. Sci. U.S.A. 86:653-656 (1989), have also synthesized cholesteryl-conjugated phosphorothioates whose anti-HIV activity is significantly greater than natural oligonucleotides with the same sequence. Additional modifications include conjugation of oligonucleotides to poly(L-lysine) alone. Stevenson, M. and Iversen, P. L. J. Gen. Virol 70:2673-2682 (1989) and Lemaitre, M., Baynard, B. and LeBleu, B. Proc. Natl. Acad. Sci. U.S.A. 84:648-652 (1987). This modification enhanced the antiviral activity of the compound studied presumably due to increased cellular uptake imparted by the polycationic poly(L-lysine).

The activity of antisense oligonucleotides previously available has not been sufficient for practical therapeutic, research or diagnostic use. The basis of this insufficiency is likely several fold i.e., (1) incomplete understanding of the secondary and tertiary structure of the targeted RNA, (2) low percentages of delivery and uptake, (3) inactivation of reactive centers by other cellular components, and (4) requirements for stoichiometric conditions for inhibition of protein production.

Enhancement of cellular uptake of antisense oligonucleotides by chemical modification would have clear advantages. Novel modifications may also lead to increased lipophilicity, greater retention, and increased distribution of the novel compounds. Increasing the concentration of oligonucleotides at specific intracellular target sites may ultimately increase the safety and efficacy of these compounds since less of the drug will be required to produce the desired effects.

Accordingly, there has been and continues to be a long-felt need for oligonucleotides and oligonucleotide analogs which are capable of effective therapeutic and diagnostic antisense use and specifically an oligonucleotide or oligonucleotide analog which is comprised of a functional group which facilitates transport into the cell and at the same time is less susceptible to nuclease activity than wild types. This longfelt need has not been satisfied by prior work in the field of antisense oligonucleotide therapy and diagnostics.

SUMMARY OF THE INVENTION

In accordance with this invention, novel types of antisense oligonucleotides are provided which are modified to enhance celluar uptake. Oligonucleotides having at least one nucleoside modified by direct attachment to a polyamine have been found to be effective in accomplishing this goal. It is preferred that the nucleoside be attached at its 5' site of the sugar moiety to the polyamine. It is preferred that the oligonucleotides in accordance with this invention be modified so as to be phosphorothioates or other backbone modified species. The oligonucleotides may preferably range in length from about 5 to about 50 nucleic acid bases. In accordance with preferred embodiments of this invention, the oligonucleotides code for the tat region of a HIV genome. In accordance with other preferred embodiments, the selected sequence coding for the tat region of the HIV genome has a thymidine at its 5' terminal end. Other preferred antisense oligonucleotide sequences include complementary sequences for herpes, papilloma and other viruses.

The modified nucleoside preferably found at the 5' end of the phosphorothioate oligonucleotide may be any pyrimidine or purine. However, preferred embodiments of this invention incorporate a modified thymidine at the 5' end.

The modified nucleosides are preferably nuclease resistant linkages of a polyamine functional group joined to the nucleoside at the 5' site of its sugar moiety. The polyamine functional group may comprise primary amines, hydrazines, semi-carbazines, thiosemi-carbazines or similar nitrogenase species. A preferred configuration of the polyamine functional group incorporates a symmetrical carbon spacing group between each amine function.

The linkage between the modified nucleoside and the polyamine functional group is preferably, generally unlike functional group additions presently known in the art. Rather than the usual phosphodiester linkage, the addition occurs directly at the 5' position. Not only is this linkage an improvement over the present state of the art because it is nuclease resistant, but in addition the direct attachment of this functional group to the oligonucleotide or oligonucleotide analog confers superior cellular uptake relative to the naturally occurring oligonucleotide. This superior cellular uptake may likely be due to the neutralizing effect that the polyamine has on the negative charges of the oligonucleotide since the polyamine may be directed back along the sugar-phosphate backbone of the oligonucleotide conjugate as well as the backbone of the polyamine-oligonucleotide heteroduplex.

This invention is also directed to methods for synthesizing such oligonucleotides such as routes comprising the synthesis of an intermediate product which may be activated to react with appropriate functional groups such as those of the above-mentioned, preferred embodiments. These methods employ the use of solid supports upon which activation takes place. Such use of the solid support may either be via a DNA synthesizer, by manual manipulation of the solid support or otherwise.

OBJECTS OF THE INVENTION

It is a principal object of the invention to provide oligonucleotide analogs for use in antisense oligonucleotide diagnostics, research reagents, and therapeutics.

It is a further object of the invention to provide nuclease resistant oligonucleotide analogs which possess enhanced cellular uptake.

Another object of the invention is to provide such oligonucleotide analogs which are therapeutically safer and which have greater efficacy than naturally-occurring antisense oligonucleotides.

It is yet another object of the invention to provide methods for synthesis of the modified oligonucleotide using solid supports.

These and other objects will become apparent to persons of ordinary skill in the art from a review of the present specification.

DETAILED DESCRIPTION OF THE INVENTION

The biological activity of the antisense oligonucleotides previously available has not generally been sufficient for practical therapeutic, research or diagnostic use. This invention directs itself to modified, naturally-occurring oligonucleotides and analogs and methods for effecting such modifications. These modified oligonucleotides and oligonucleotide analogs, exhibit increased biological activity relative to their naturally-occurring counterparts. Furthermore, these modifications may be effected using solid supports which may be manually manipulated or used in conjunction with a DNA synthesizer using methodology commonly known to those skilled in the art.

In the context of this invention, the term "oligonucleotide" refers to a plurality of joined nucleotide units formed in a specific sequence from naturally occurring bases and furanosyl groups joined through a sugar group by native phosphodiester bonds. These nucleotide units may be nucleic acid bases such as guanine, adenine, cytosine, thymine or uracil. The sugar group may be a deoxyribose or ribose. This term refers to both naturally occurring or synthetic species formed from naturally occurring subunits.

"Oligonucleotide analog" as the term is used in connection with this invention, refers to moieties which function similarly to oligonucleotides but which have non naturally occurring portions. Oligonucleotide analogs may have altered sugar moieties or inter-sugar linkages, for example, phosphorothioates and other sulfur containing species which are known for use in the art. Oligonucleotide analogs may also comprise altered base units or other modifications consistent with the spirit of this invention, in order to facilitate antisense therapeutic, diagnostic or research reagent use of a particular oligonucleotide.

In accordance with the invention, an oligonucleotide sequence is generally chosen which is complementary to DNA or RNA which is involved in the production of proteins whose synthesis is ultimately to be modulated or inhibited in entirety. One preferred embodiment of this invention is an antisense oligonucleotide analog complementary to the DNA or RNA which codes for the tat region of HIV. Other preferred embodiments are directed to herpes and papilloma viruses and still others will be apparent to persons of ordinary skill in the art.

Also in accordance with preferred embodiments of this invention, phosphorothioate bonds are substituted for the phosphodiester bonds which normally comprise the sugar phosphate backbone of oligonucleotides. These oligonucleotide analogs are preferably further modified at their terminal 5' end by the addition of a nucleoside analog. This nucleoside analog is most preferably a modified thymidine. Said modified nucleoside is so modified by the addition of a protecting group such as at the 5' site of the sugar moiety of the thymidine. The protecting group in accordance with one preferred embodiment of this invention is a 1,3 diphenylimidazolynyl group.

Figure 1:
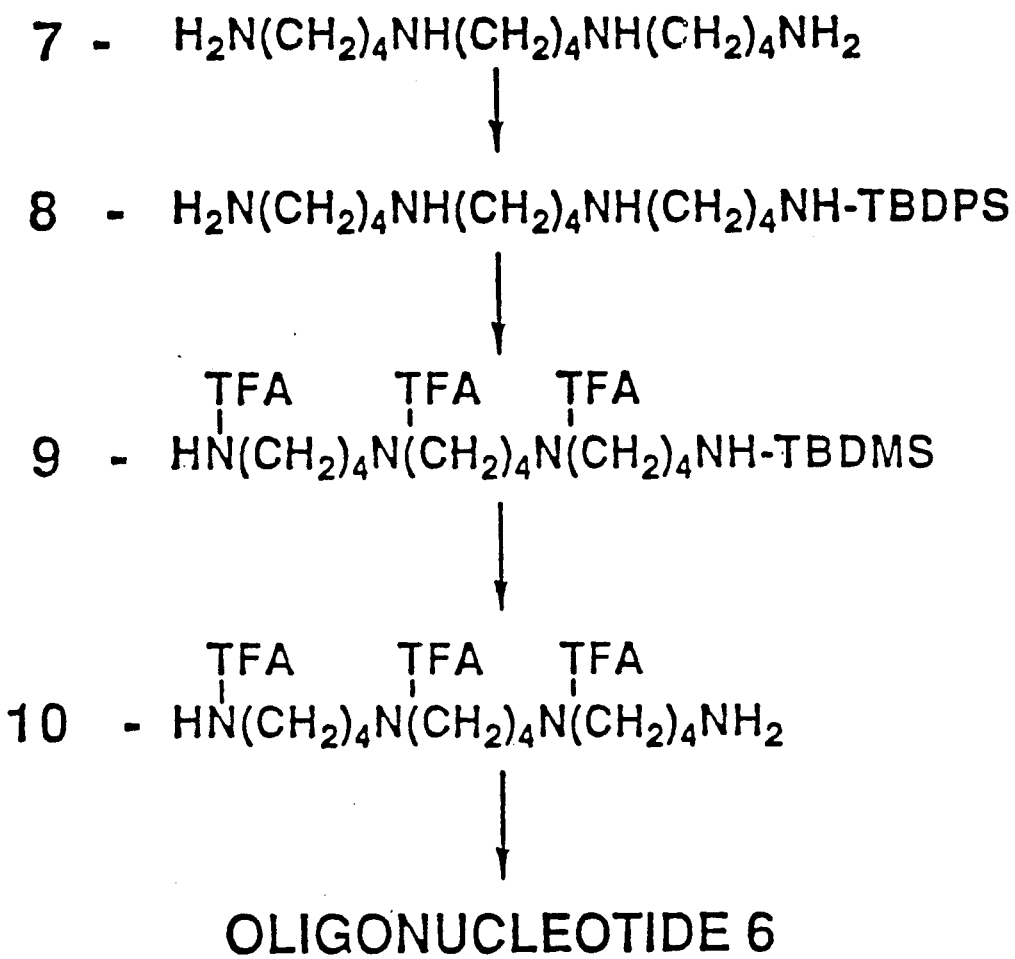
FIG. 1 is a flow chart of certain synthetic schemes useful for the synthesis of some polyamine functional groups useful in the practice of this invention.

The modified nucleoside analog, having been incorporated into the oligonucleotide analog, is preferably further modified by the replacement of the protecting group at the 5' site of its sugar moiety with a nitrogenous functional group. The nitrogenous functional group is preferably a polyamine such as any of primary polyamines, amines, hydrazines, semicarbazides, or thiosemicarbazides but which preferably is a polyamine having the structures of polyamine 8 or polyamine 10 as set forth in FIG. 1. The intermediate Schiff base or imine or semicarbazones are reduced to the substituted amine or hydrazine. Most preferable the nitrogenous functional group has the structure of polyamine 10 as set forth in FIG. 1.

Accordingly, preferred polyamines have the general formula:

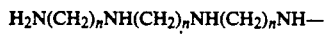

wherein n is an integer between 2 and 6. It is preferred that n be 4.

In accordance with this invention, polyamines, which are positively charged, are caused to lie along the negatively charged sugar-phosphate backbone of the oligonucleotide. This configuration is believed to neutralize the negative charges of the oligonucleotide and enhance the cellular penetration of the oligonucleotide. Several recent reports have suggested that a polyamine may form hydrogen bonds to the edges of the base pairs in the major groove. Loke, S. L., Stein, C. A., Zhang, X. H., Mori, K., Nakanishi, M., Subashinghe, G., Cohen, J. S. and Neckers, L. M. Proc. Natl. Acad. Sci. U.S.A. 86:3473-3479 (1989). To avoid this problem, this invention preferably does not employ the usual phosphodiester conjugation linkage but instead attaches the polyamine directly to the 5' position. By eliminating the phosphodiester bond as the conjugation linker and attaching the polyamine directly to the 5' position, there is believed to be a strong tendency to direct the polyamine chain back along the sugar phosphate backbone of the oligonucleotide conjugate as well as along the backbone of the polyamine-oligonucleotide heteroduplex.

Preferred embodiments of this invention employ a polyamine containing about four carbon units between each amine. Carbon spacers may be arranged in a variety of configurations in relation to the amine groups. This arrangement may be useful in directing the site residence of the polyamine on the oligonucleotide and its heteroduplex. This ability to direct a polyamine to reside at certain positions of the attached oligonucleotides and their heteroduplexes will likely have an important bearing on oligonucleotide uptake and other oligonucleotide properties. Other carbon unit numbers may be included among the nitrogen atoms of the preferred polyamines in accordance with this invention. Persons of ordinary skill in the art will have wide latitude in selecting optimum configurations for particular circumstances, two, five, six or other numbers of carbon units may be employed.

Figure 2:
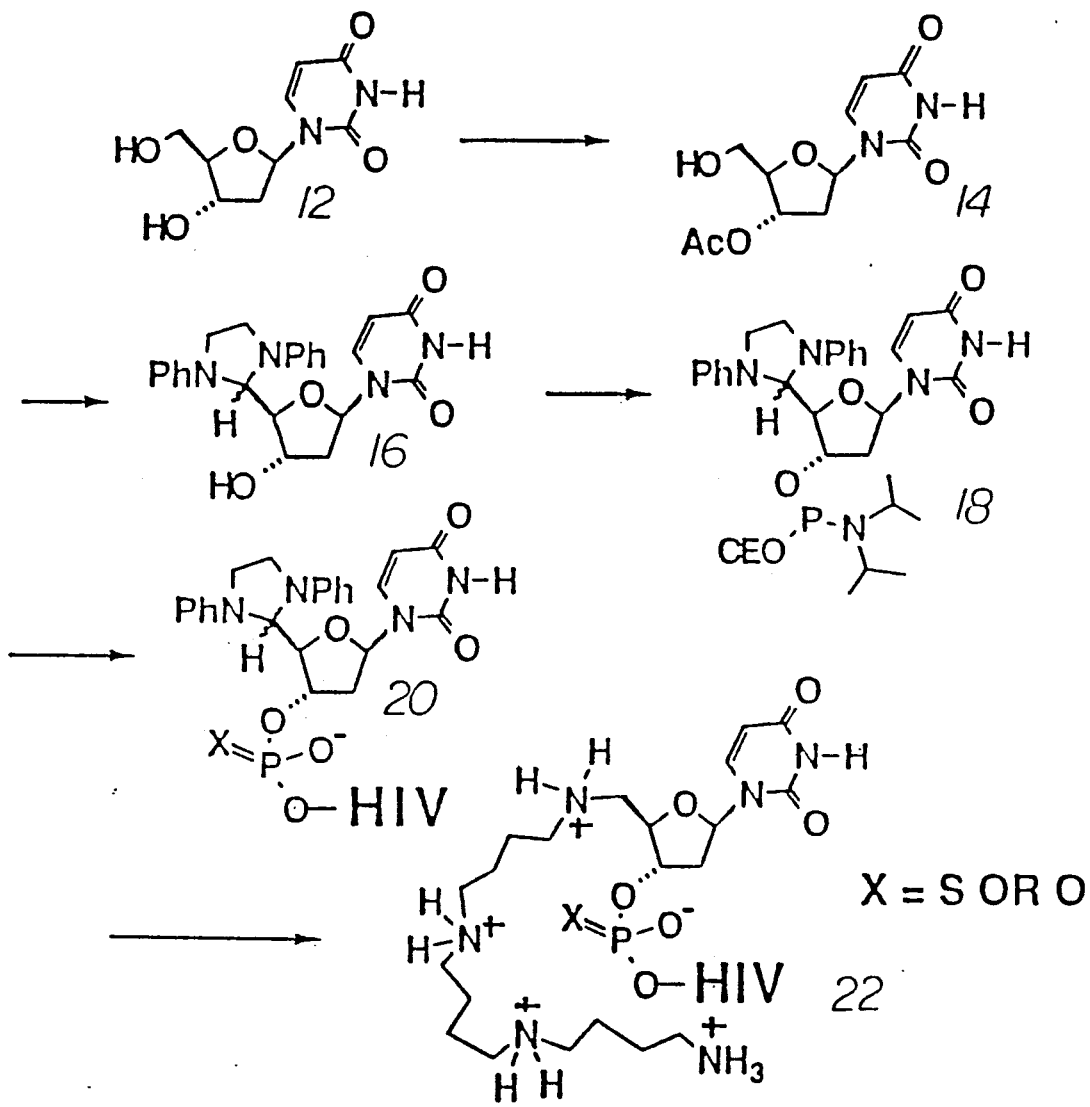
FIG. 2 sets forth one method for the synthesis of polyamine conjugated phophorothioate oligonucleotides useful in this invention.

In accordance with certain aspects of the invention, FIG. 2 sets forth one chemical synthesis of modified phosphoramidite oligonucleotide analogs. In particular, FIG. 2 sets forth novel processes involving the synthesis of 1,3 diphenylimidazolidine protected 5' aldehydic-3'-(2-cyanoethyl N,N diisopropylphosphoramidityl) thymidine. This base-stable thymidine analog is placed at the 5' end of a desired oligonucleotide sequence and is activated as needed to couple polyamines such as primary amines, hydrazines, semi-carbazides, or thiosemicarbazides.

The starting material employed by the method set forth in FIG. 2 is deoxyribofuranosyl and ribofuranosyl-nucleosides which can be prepared in high yields by the procedure of, or obvious modification of the procedure of, Pfitzner and Moffatt where the oxidation of 3'-acetyl thymidine is described. Pfitzner, K. E. et al., J. American Chem. Soc. 85: 3027 (1963). The acetyl derivative of the nucleoside to be modified may also be a suitable starting material and may be commercially available or may be prepared by a three step process using procedures known to those skilled in the art.

The first step of this process is the addition of t-butyl-dimethylsilyl chloride (TBDMSCl) to the selected nucleoside. Second, Ac$_2$O is added, followed by the addition of Bu$_4$F to produce the final acetyl derivative of a selected nucleoside. In accordance with the preferred embodiment of this invention, the starting material, thymidine, is converted to 3'-acetyl thymidine, using the three step process, or alternatively, 3'-acetyl thymidine is commercially available.

The 3'-acetyl nucleoside (14) is subsequently oxidized by treatment with DMSO/DCC followed by treatment with 1,2 dianilinoethane to produce 3'-O-acetyl-5'-deoxy-5'-(1,3-diphenylimidazolin-2-yl) nucleoside (16). This protecting group has been found to be stable to basic conditions and can be hydrolyzed back to an aldehyde with mild acid. Any of the existing or yet to be discovered groups useful in accomplishing this function may be employed in accordance with the practice of the present invention. In accordance with preferred embodiments the protected species resulting from the treatment of the 3'-acetyl thymidine with DMSO/DCC followed by treatment with 1,2 dianilinoethane was 3'-O-acetyl-5'-deoxy-5'-(1,3-diphenylimidazolin-2-yl) thymidine. The protected nucleoside is next transformed to a phosphoramidite (18) by standard procedures of base deprotection through the addition of NH$_3$/MeOH and subsequent phosphitylation by the addition of phosphityl Cl. The preferred method being phosphitylation by the addition of 2-cyanoethyl N,N diisopropylchlorophosphoramidite to produce diphenylimidazolinylthymine phosphoramidite.

Separately, a phosphorothioate oligonucleotide having a preselected sequence is extended on a solid support in a 5' direction until such point at which a nucleoside corresponding to the specific modified nucleoside prepared above need be incorporated into the oligonucleotide sequence. The modified nucleoside is substituted for its naturally occurring terminal nucleoside counterpart (20). Most preferably a modified thymidine replaces its naturally occurring counterpart at the 5' end. Synthesis may be carried out conveniently through solid state synthesis employing known phosphoramidite methodology on a DNA synthesizer or otherwise. Nucleic acid synthesizers are commercially available and their use is generally understood by persons of ordinary skill in the art as being effective in generating nearly any oligonucleotide of reasonable length which may be desired. Such oligonucleotide chain may be from about 5 to about 50 nucleic acid bases in length. It is more preferred that such functionalities have from 8 to about 40 base units and even more preferred that from about 12 to 20 base units be employed. At present, it is believed that oligonucleotide analogs having about 15 base units will likely be found to be best for the practice of certain embodiments of the present invention.

According to a preferred embodiment of this invention, the tat region of HIV is extended in the 5' direction to produce the sequence CCGCCCCTCGCCTCTTGCCT because this region is believed to have the most potent activity in inhibiting the expression of the tat protein. See U.S. Pat. Ser. No. 521,907, incorporated by reference, filed May 11, 1990 and assigned to the Assignee of this invention. The sequence is then preferably extended three additional nucleotides to TCGCCGCCCCTCGCCTCTTGCCT in order to allow for a T nucleotide on the 5' end. The thymine residue was substituted with a diphenylimidazolinylthymidine as described above.

The resulting phosphoramidite linkage may be preferably sulfurized using the known Beaucage reagent, Beaucage, S. L. et al., J. Am. Chem. Soc. 112:1253-1254 (1990), to afford preferred phosphorothioates, or by iodine to afford the phosphodiester linkage.

The addition of a nitrogenous functional group, preferably a polyamine such as those incorporating primary amines, hydrazines, semicarbazides, or thiosemicarbazides, may be preferably effected once the modified nucleoside has been added to the phophoramidite oligonucleotide. The first step in this addition is the deprotection of the modified nucleoside which has been added to the 5' end of the oligonucleotide. This deprotection can occur, according to preferred embodiments by treatment of the control pore glass (CPG) support (which binds the phosphoramidite oligonucleotide in the synthesizer) with 3% dichloroacetic acid (DCA) in THF. Thereafter, the CPG support is treated with a polyamine so as to form a Schiff's base which is reduced to an amine by the addition of sodium cyanoborohydride ($NaCHBH_3$). Finally the column is treated with ammonium hydroxide to deprotect and remove the polyamine-oligonucleotide conjugate (22) from the support. Treatment of the CPG support may be effected by a DNA synthesizer or manually using syringes. The preferred functional groups for the embodiment of this invention are polyamines. Most preferably, the polyamine functional group useful in combination with other preferred components of this invention, is tris-(aminobutyl)amine. This polyamine was chosen because of preferred length. The length of these amine-carbon linkages approximately spans the length of a 15 base pair oligonucleotide based upon molecular modeling. Carbon spacers placed between each amine may be useful in directing the polyamine to reside at certain positions of the attached oligonucleotide. Preferably, carbon spacers will be arranged such that the carbon spacing group will be symmetrical. Four carbon spacers placed between each amine is a preferred embodiment of this invention.

Synthesis of the polyamine group may be performed by procedures known in the art. For preferred embodiments, the synthesis of the polyamine group can be performed according to the steps set forth in FIG. 1. The synthesis of tris(aminobutyl)amines (7) can be obtained by procedures described by Niitsu and Samejima, Chem. Pharm. Bull. 34(3):1032-1038 (1986), incorporated by reference herein. Such amines will be protected such as with a t-butyldiphenylsilyl group at one of the primary amines according to the procedure set forth by Miller and Braiterman, et al., Biochemistry 16:1988-1996 (1977), which involves the addition of TNDPS-Cl and $Et_3N$. The resulting t-butyl diphenyl silyamine (8) is a convenient amine for reaction with the modified oligonucleotide. More preferably, however, this compound will be further modified by trifluoroacetylation with trifluoroethyl acetate in $Et_2N$ to produce polyamine 9 (9) followed by selective removal of the t-butyldiphenylsilyl moiety with pyridinium hydrogen fluoride to provide a protected amine (10). This deprotection process is described by Overman, et al, Tetrahedron Lett. 27:4391-4394 (1986). The overall process, is amendable to the synthesis of a wide variety of polyamine in high overall yield. All mentioned references are incorporated by reference herein.

In the alternative, the 5' aldehyde of a nucleoside may be condensed with a trifluoroacetyl protected polyamine. Subsequent reduction of the Schiff's base with sodium cyanoborohydride and phosphitylation of the 3' position will afford a protected polyamine monomer. This protected polyamine monomer may be attached to the 5' end of the oligonucleotide via the DNA synthesizer.

Deprotection and removal of the polyamineoligonucleotide conjugate from the column may be performed by treatment of the column with ammonium hydroxide. Finally, the composition may be purified using HPLC and gel electrophoresis systems. Such purification procedures are well known by those skilled in the art.

•The following examples are illustrative, but not limiting, of the invention.

EXAMPLE 1

Preparation of 1,3 Diphenylimidazolynyl

3' acetyl thymidine, prepared through standard procedures known in the art, was treated with DMSO/DCC. This treatment was followed by treatment of the mixture with dianilinoethane to produce 3'-O-acetyl 5' deoxy-5' (1,3-diphenylimidazolin-2-yl)thymidine according to procedures of Pfitzner and Moffatt.

2. Phosphoramidite Production

3'-O-acetyl 5' deoxy 5' (1,3 diphenylimidazolin-2-yl)thymidine was transformed to the phosphoramidite using standard procedures of base deprotection and followed by phosphitylation to produce 2-cyanoethyl N,N-diisopropylchlorophosphoramidite.

3. Preparation of Oligonucleotide Sequence

Extend the active HIV phosphorothioate oligonucleotide with the sequence 5'

CCGCCCCTCGCCTCTTGCCT 3' (464A) in the 5' direction until a thymidine residue was encountered. The addition of three additional nucleotides to produce an oligonucleotide of the sequence 5' TCGCCGCCCCTCGCCTCTTGCCT 3' was performed by standard automated synthesis on an ABI model 380B DNA synthesizer. The terminal thymidine was then replaced by diphenylimidazolinylthymidine.

4. Preparation of Polyamine

Prepared tris (aminobutyl)amine for addition to the oligonucleotide by standard procedures known to those skilled in the art.

5. Addition of Polyamine

The phosphoramidite linkage was sulfurized with Beaucage reagent. Beaucage, S. L. et al., J. Am. Chem. Soc. 112: 1253–1254 (1990). Next, the CPG support was treated with 3% dichloroacetic acid in THF. The CPG support was subsequently treated with tris(trifluoroacetyl)tris(aminobutyl)amine to form Schiff's base. Sodium cyanoborohydride (NaCNBH$_3$) was added to reduce the conjugate to an amine. The column was treated with ammonium hydroxide to deprotect and remove the conjugate from column support. The polyamine conjugate was purified with ion exchange HPLC, using a Beckman Gold HPLC system, and with gel electrophoresis.

EXAMPLE 2

Using the protocol set forth in Example 1, the synthesis of an antisense phosphoramidite oligonucleotide of papilloma virus mRNA cap region, 5' TATGCAAGTACAAAT 3', is performed.

EXAMPLE 3

Using the protocol set forth in Example 1, the synthesis of an antisense phosphoramidite oligonucleotide of papilloma virus mRNA cap region, 5' TATGCAAGTACAAAT 3', is performed.

EXAMPLE 4

Using the protocol set forth in Example 1, the synthesis of an antisense phosphoramidite oligonucleotide of papilloma virus initiation of translation sequence, 5' TCTCCATCCTCTTCACT 3', is performed.

EXAMPLE 5

Using the protocol set forth in Example 1, the synthesis of an antisense phosphoramidite oligonucleotide of herpes virus, 5' TCATCCATCCTTCGGCC 3', is performed.

EXAMPLE 6

Using the protocol set forth in Example 1, the synthesis of an antisense phosphoramidite oligonucleotide of herpes virus 5' TGGCCATTTCAACAGA 3', is performed.

EXAMPLE 7

Using the protocol set forth in Example 1, the synthesis of an antisense phosphoramidite oligonucleotide of herpes virus 5' TCATCCATCCGTCCGCC 3', is performed.

EXAMPLE 8

Using the protocol set forth in Example 1, the synthesis of an antisense phosphoramidite oligonucleotide of herpes virus 5' TTGGCCATTGGAACCAA 3', is performed.

What is claimed is:

1. An oligonucleotide analog having at least one nucleoside modified by direct attachment of a polyamine at the 5' site of its sugar moiety.

2. The oligonucleotide analog of claim 1 wherein the oligonucleotide analog ranges in length from about 5 to about 50 nucleotide base unit.

3. The oligonucleotide analog of claim 1 wherein said nucleoside is thymidine.

4. The oligonucleotide analog of claim 1 wherein said polyamine is a primary amine, a hydrazine, a semicarbazide, or a thiosemicarbazide.

5. The oligonucleotide analog of claim 1 specifically hybridizable with the tat region of an HIV genome.

6. The oligonucleotide analog of claim 5 wherein said selected sequence has a thymidine at its 5' terminal end.

7. The oligonucleotide analog of claim 1 specifically hybridizable with a selected portion of a herpes genome.

8. The oligonucleotide of claim 1 specifically hybridizable with a selected portion of a papilloma genome.

9. the oligonucleotide analog of claim 1 wherein said polyamine has the structure:

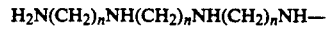

$H_2N(CH_2)_nNH(CH_2)_nNH(CH_2)_nNH-$ wherein n is an integer between 2 and 6.

10. The oligonucleotide analog of claim 9 wherein n is 4.

11. The oligonucleotide analog of claim 1 comprising at least one phosphorothioate group.

* * * * *

UNITED STATES PATENT AND TRADEMARK OFFICE
CERTIFICATE OF CORRECTION

PATENT NO. : 5,138,045

DATED : August 11, 1992

INVENTOR(S) : Phillip D. Cook, Charles J. Guinosso

It is certified that error appears in the above-identified patent and that said Letters Patent is hereby corrected as shown below:

<u>TITLE PAGE</u>
Line 6 of the Abstract, delete tat and replace with <u>tat</u>

Col. 1, line 47, add "and" after biological and before antiviral

Col. 10, line 34, in claim 5 underline "<u>tat</u>"

Signed and Sealed this

Tenth Day of May, 1994

Attest:

BRUCE LEHMAN

Attesting Officer

Commissioner of Patents and Trademarks